United States Patent [19]

D'Amico

[11] 4,447,618
[45] May 8, 1984

[54] N-SUBSTITUTED THIOXOBENZOTHIAZOLINES

[75] Inventor: John J. D'Amico, Olivette, Mo.

[73] Assignee: Monsanto Company, St. Louis, Mo.

[21] Appl. No.: 55,103

[22] Filed: Jul. 5, 1979

[51] Int. Cl.³ .......................................... C07D 277/70
[52] U.S. Cl. .................................... 548/170; 548/171; 71/90
[58] Field of Search ............................ 548/170, 171

[56] References Cited

U.S. PATENT DOCUMENTS 3,839,349 10/1974 Wagner et al. .................. 548/170

OTHER PUBLICATIONS

Sohav et al., J. Het. Chem., 6, pp. 163–174, (1969).

Primary Examiner—Paul M. Coughlan, Jr.
Assistant Examiner—D. B. Springer
Attorney, Agent, or Firm—Richard H. Shear; Patricia A. Coburn; Raymond C. Loyer

[57] ABSTRACT

The present invention relates to compounds of the formula

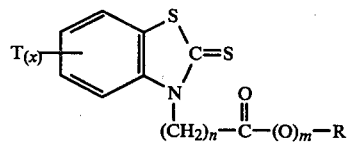

wherein:

T is hydrogen, lower alkyl, halo, —$CF_3$, —CN or —$NO_2$; x is 1 or 2; n is 1 or 2; m is zero or 1; when m is 1, R is hydrogen, lower alkyl, halo (lower) alkyl, lower alkenyl, halo (lower) alkenyl, benzyl, phenyl, carbamoyl (lower) alkyl, cyano (lower) alkyl or agriculturally acceptable salts; when m is zero, R is

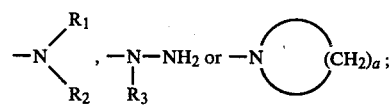

$R_1$ and $R_2$ independently equal hydrogen, lower alkyl, lower alkenyl, lower alkoxy (lower) alkyl or phenyl; $R_3$ is hydrogen or lower alkyl; a is 4, 5 or 6.

4 Claims, No Drawings

N-SUBSTITUTED THIOXOBENZOTHIAZOLINES

BACKGROUND OF THE INVENTION

This invention relates to new N-substituted thioxobenzothiazolines and to their use as leguminous plant growth regulants as well as to plant growth regulant compositions.

As the world population continues to grow, there is increasing need to produce food and to produce it more efficiently. Leguminous plants, especially soybean plants, play an important role in the world's total food supply. Soybeans, for example, are processed for meal and oil in all continents of the world except Antarctica. Currently, wordl soybean production accounts for the majority of the total world oil seed production. Soybean proteins are a major source of the protein in feed that is converted into animal proteins such as meat, milk and eggs. Increasingly, soybean protein is being used directly to replace traditional animal proteins. There can be no doubt that leguminous crop plants, especially soybeans are extremely valuable food sources. Using leguminous plant growth regulators to control the internal metabolism of the crop plant offers an important means of increasing crop yield to meet the world demand for food materials.

DESCRIPTION OF THE INVENTION

The invention relates to a new class of chemical compounds and their use as plant growth regulants. More specifically, the invention relates to novel N-substituted thioxobenzothiazoline derivatives useful in regulating the growth of leguminous plants.

N-substituted thioxobenzothiazolines useful in accordance with this invention are represented by the formula

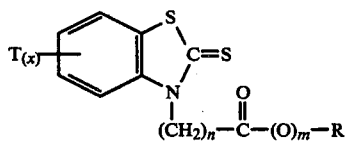

wherein:
T is hydrogen, lower alkyl, halo, —CF$_3$, —CN or —NO$_2$;
x is 1 or 2;
n is 1 or 2;
m is zero or 1;
when m is 1, R is hydrogen, lower alkyl, halo (lower) alkyl, lower alkenyl, halo (lower) alkenyl, benzyl, phenyl, carbamoyl (lower) alkyl, cyano (lower) alkyl or agriculturally acceptable salts;
when m is 0, R is

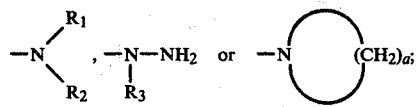

R$_1$ and R$_2$ independently equal hydrogen, lower alkyl, lower alkenyl, lower alkoxy (lower) alkyl or phenyl; R$_3$ is hydrogen or lower alkyl; a is 4,5 or 6.

Except where m is one and R is equal to hydrogen or ethyl, the compounds of the above formula are believed to be novel.

In the description of the novel N-substituted thioxobenzothiazoline derivatives useful as plant growth regulants according to this invention, the following embodiments are intended for the various groups.

Where the expression "lower" is employed in conjunction with terms, such as for example, alkyl, haloalkyl, cyanoalkyl, carbamoylalkyl or alkoxy, it is intended to indicate that the alkyl portion of the substituent group has a carbon content of 1 to 5 carbon atoms. Typically alkyl includes those members including straight and branched chain, as for example, methyl, ethyl, n-propyl, isopropyl, n-butyl, sec-butyl, tert-butyl, n-pentyl, isopentyl, and the like.

Typically, alkoxy includes those members, as for example, methoxy, ethoxy, propoxy, butoxy, tert-butoxy, pentoxy and the like. The term "halo" or "halogen" when used herein refers to chlorine, bromine, fluorine or iodine atoms. The term "halo (lower) alkyl" is used herein to refer to such substituent groups, as for example, chloromethyl, chloroethyl, bromoethyl, etc.

Where the expression "lower" is employed in conjunction with the term alkenyl or haloalkenyl, it is intended to indicate that the alkenyl portion of the substituent group has a carbon content of 2 to 5 carbon atoms and preferably 3 to 5 carbon atoms and most preferably 3 carbon atoms. Typically alkenyl includes such groups as ethenyl, 1-propenyl, methyl-2-propenyl, 2-methyl-2-propenyl, 2-butenyl, 1-methyl-2-butenyl, 2-methyl-2-butenyl, 3-butenyl, 1-methyl-3-butenyl or 2-methyl-3-butenyl and the like.

The term "carbamoyl" is used herein to refer to the aminocarbonyl radical having the structure

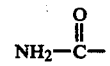

The radical represented by the formula

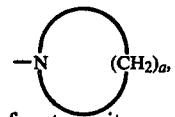

where a is 4 to 6, refers to a nitrogen-containing heterocycle containing 4 to 6 carbon atoms, e.g., pyrrolidinyl, 1-piperidinyl or hexamethyleneimino.

By the term "agriculturally-acceptable salts", is meant any salt or salt-like derivative which preserves the activity, or substantially the activity, of the parent (that is, unsalified) compound, and which has no additional, undesirable effect on the plant being treated. It is to be understood that in some instances such salts may display an enhanced activity due to their being more readily assimilated by the plant being treated. Examples of the commonly employed salts are the metal salts of the acid function—such as the salts with sodium, calcium, zinc, potassium and lithium—amine salts of the acid function—such as a methylammonium, ethylammonium, diethylammonium, triethanolamine, and the like. There are a very large number of agriculturally acceptable salts suitable for use in this invention as would readily be appreciated by one skilled in the art.

Particularly contemplated within the scope of the present invention are those compounds wherein m is equal to 1. In this case, the compounds of the invention have the formula:

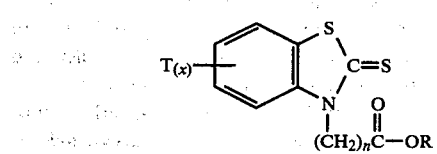

where T, x, n and R have the meanings previously described.

Within this group of compounds, R may equal hydrogen, lower alkyl, halo (lower) alkyl, lower alkenyl, halo (lower) alkenyl, benzyl, phenyl, carbamoyl (lower) alkyl, cyano (lower) alkyl, agriculturally acceptable salts or any combination of these moieties. Such a combination, as for example wherein R is equal to halo (lower) alkyl, lower alkenyl or halo (lower) alkenyl, wherein R is equal to hydrogen, lower alkyl, benzyl or phenyl, wherein R is equal to phenyl, carbamoyl (lower) alkyl or cyano (lower) alkyl, and the like are expressly contemplated herein.

Also particularly contemplated within the scope of the present invention are those compounds wherein m is equal to zero. In this case, the compounds of the invention have the formula:

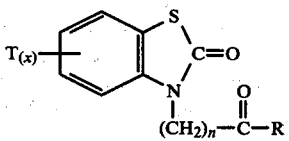

where T, x, n and R have the meanings previously described.

Within this group of compounds R may equal

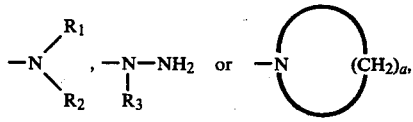

where $R_1$, $R_2$, $R_3$ and a have the meanings previously described. Preferred are those compounds formed when R is equal to

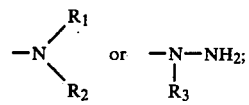

particularly preferred are those compounds formed when R is equal to

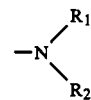

Within the subclass formed when R is

$R_1$ and $R_2$ may independently equal hydrogen, lower alkyl, lower alkenyl, lower alkoxy (lower) alkyl or phenyl. It is expressly contemplated herein that $R_1$ and $R_2$ may also equal any combination of the aforementioned groups. Such a combination, as for example, where $R_1$ and $R_2$ equal hydrogen, lower alkyl or lower alkenyl, wherein $R_1$ and $R_2$ equal lower alkyl, lower alkoxy (lower) alkyl or phenyl, wherein $R_1$ and $R_2$ are equal to hydrogen, lower alkenyl or phenyl, and the like are expressly contemplated herein.

The compounds of this invention are prepared according to several methods. These methods are illustrated by the following reaction schemes:

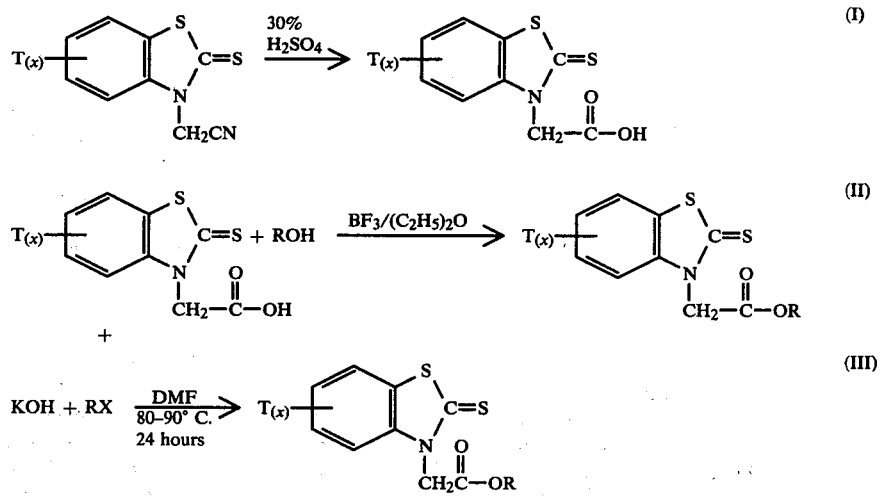

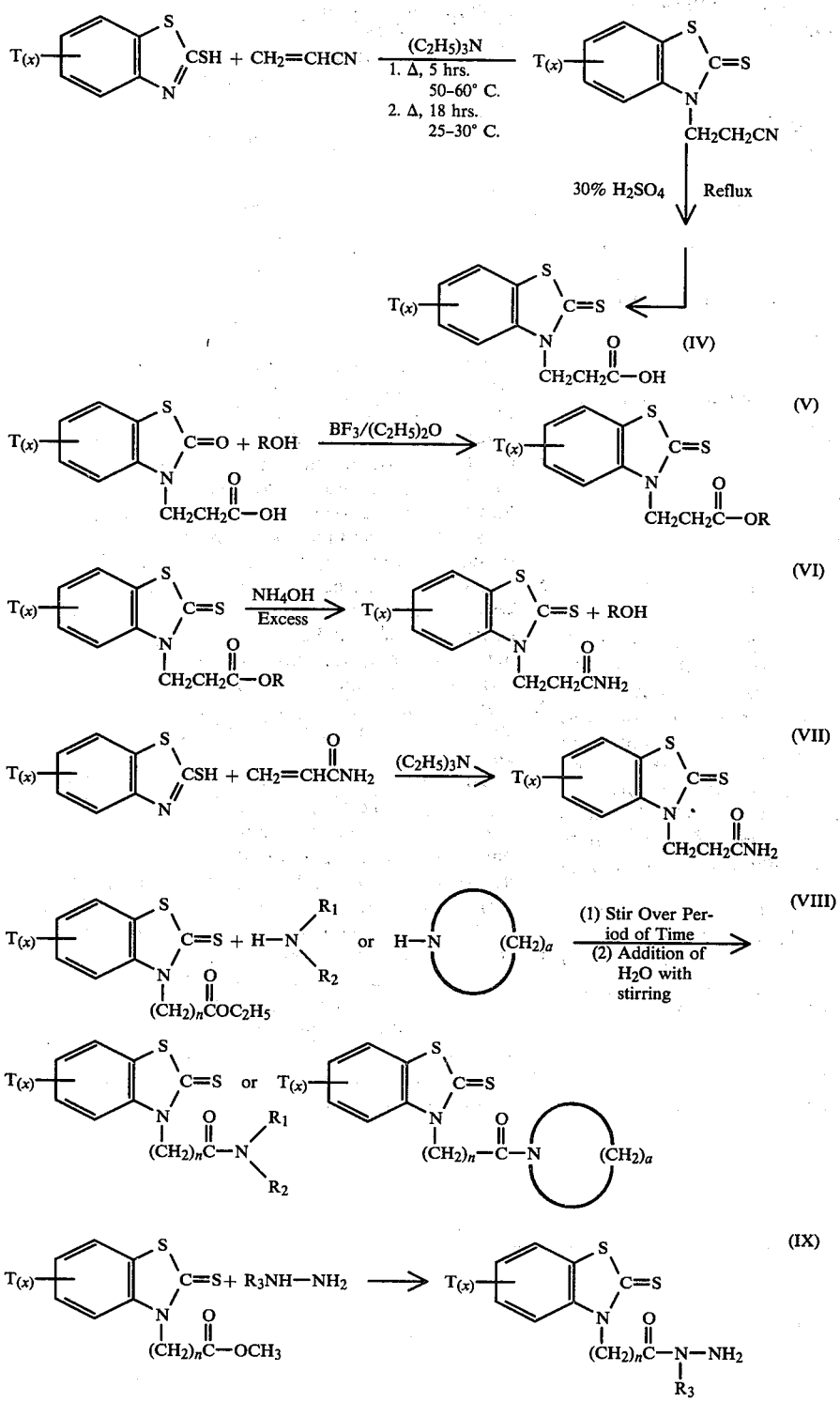

Unless otherwise indicated, T, x, n, a, $R_1$, $R_2$ and $R_3$ are defined as was previously described.

The following examples describe in detail the preparation of the compounds of this invention; these examples are presented merely as illustration, since it will be apparent to those skilled in the art that many modifications both of materials and methods may be practiced within the spirit and scope of the present disclosure.

EXAMPLE 1

Preparation of 2-Thioxo-3(2H)-Benzothiazoleacetic Acid, Ethyl Ester

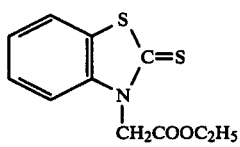

The compound of Example 1 was prepared according to the procedure described by C. H. Chen, ORGANIC PREPARATIONS AND PROCEDURES, Inst. 8(1), 1-5 (1976).

EXAMPLE 2

Preparation of 2-Thioxo-3(2H)-Benzothiazoleacetic Acid

A stirred slurry containing 10.3 g (0.05 mol) of 2-thioxo-3-benzothiazolineacetonitrile and 150 ml of 30% sulfuric acid (by volume) was heated at reflux for 2 hours. After cooling to 25° C., 800 ml of water was added and stirring was continued for 30 minutes at 25°-30° C. The solid was collected by filtration, washed with water until neutral to litmus, and air-dried at 25°-30° C. The product, 2-thioxo-3(2H)-benzothiazoleacetic acid was obtained in 90% yield, m.p. 187°-189° C. After recrystallization from 1,2-dichloroethane the crystals melted at 192°-193° C.

Anal. Calc'd for $C_9H_7NO_2S_2$: C, 47.98; H, 3.13; N, 6.22; S, 28.46. Found C, 47.73; H, 3.16; N, 6.30; S, 28.57.

The compound of Example 2 may also be prepared according to the procedure described by C. H. Chen, ORGANIC PREPARATIONS AND PROCEDURES, Inst., 8(1) 1-5 (1976).

EXAMPLE 3

Preparation of 2-Thioxo-3(2H)-Benzothiazoleacetic Acid, Sodium Salt

To 11.3 g (0.05 mol) of the compound of Example 2 was added 4.0 g (0.05 mol) of 50% sodium hydroxide and 100 ml of water with stirring. An aqueous (10.7%) solution of 2-thioxo-3(2H)-benzothiazoleacetic acid, sodium salt was obtained.

EXAMPLE 4

Preparation of 2-Thioxo-3(2H)-Benzothiazoleacetic Acid, Methyl Ester

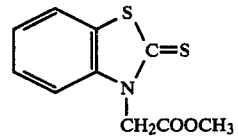

To a stirred solution containing 45.1 g (0.2 mol) of 3-(carboxymethyl) benzothiazoline-2-thione in 600 ml of methyl alcohol, 142.0 g (1.0 mol) of boron trifluoride ether complex was added in one portion. An exothermic reaction set in causing a temperature rise from 20° to 37° C. The stirred solution was heated at reflux for 24 hours and then cooled to 0° C. After cooling, 1400 ml of 10% aqueous sodium bicarbonate was slowly added (foaming observed) at 0°-10° C. until pH 8 was obtained. After stirring at 0°-10° C. for one hour, the solid was collected by filtration, washed with water until neutral to litmus and air-dried at 25°-30° C. The product, 2-thioxo-3(2H)-benzothiazoleacetic acid, methyl ester was obtained in 94% yield, m.p. 127°-128° C.

Anal. Calc'd for $C_{10}H_9NO_2S_2$: C, 50.19; H, 3.79; N, 5.85; S, 26.80. Found: C, 50.08; H, 3.84; N, 5.83; S, 26.74.

The compounds shown in Table 1 were prepared according to the following procedure:

A charge containing 22.5 g (0.1 mol) of the compound of Example 2, 6.6 g (0.1 mol) of 85% potassium hydroxide, 200 ml of DMF and 10.0 ml of water was stirred for 10 minutes. To the stirred slurry, the appropriate halogen compound was added in one portion and heated for 24 hours at 80°-90° C. After cooling to 5° C., 800 g of ice water and 25 ml of ethyl ether were added and stirring was continued for 2 hours at 0°-10° C. The ester was collected by filtration, washed with water until neutral to litmus and air-dried at 25°-30° C. The data are summarized in Table I. In the case of the compounds shown in Table I, T is hydrogen and x is 1.

TABLE I

| Ex. No. | R | X | % Yield | M.P. % C | % C Calc'd | % C Found | % H Calc'd | % H Found | % N Calc'd | % N Found | % S Calc'd | % S Found |
|---|---|---|---|---|---|---|---|---|---|---|---|---|
| 5 | —CH$_2$CH=CH$_2$ | Br | 98 | 86-8[a] | 54.32 | 54.40 | 4.18 | 4.22 | 5.28 | 5.29 | 24.17 | 24.09 |
| 6 | —CH$_2$C$_6$H$_5$ | Br | 76 | 118-20[b] | 60.93 | 60.86 | 4.15 | 4.18 | 4.44 | 4.45 | 20.33 | 20.28 |
| 7 | —CH$_2$CCl=CCl$_2$[e] | Cl | 51 | 95-6[a] | 39.09 | 39.11 | 2.19 | 2.22 | 3.80 | 3.83 | 17.39 | 17.37 |
| 8 | —CH$_2$C(O)—NH$_2$ | Cl | 31 | 177-9[c] | 46.79 | 46.59 | 3.57 | 3.60 | 9.92 | 9.82 | 22.71 | 22.65 |

TABLE I-continued

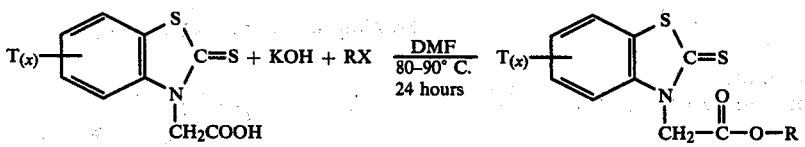

| Ex. No. | R | X | % Yield | M.P. % C | % C Calc'd | Found | % H Calc'd | Found | % N Calc'd | Found | % S Calc'd | Found |
|---|---|---|---|---|---|---|---|---|---|---|---|---|
| 9 | —CH₂CN | Cl | 85 | 172-4[d] | 49.98 | 50.03 | 3.05 | 3.08 | 10.60 | 10.60 | 24.26 | 24.22 |

[a]Recrystallization from methyl alcohol
[b]Recrystallization from isopropyl alcohol
[c]Recrystallization from isopropyl alcohol/DMF (5:1)
[d]Recrystallization from ethyl acetate
[e]Calc'd Cl: 28.85 Found: 28.96

EXAMPLE 10

Preparation of 2-Thioxo-3(2H)-Benzothiazolepropenoic Acid

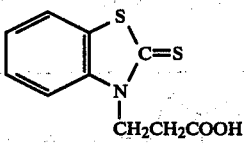

To a stirred solution containing 103.2 g (0.6 mol) of 2-mercaptobenzothiazole, 60.8 g (0.6 mol) of triethylamine and 750 ml of water, all at 50° C., was added 37.1 g (0.7 mol) of acrylonitrile in one portion. The stirred reaction mixture was heated for five hours at 50°-60° C. and thereafter for 18 hours at 25°-30° C. The product, 2-thioxo-3-benzothiazolinepropionitrile was collected by filtration, washed with water until neutral to litmus, and air-dried at 25°-30° C., yield 96%, m.p. 167°-168° C. After recrystallization from ethyl acetate, the crystals melted at 168°-169° C.

Anal. Calc'd for $C_{10}H_8N_2S_2$: C, 54.52; H, 3.66; N, 12.72; S, 29.11. Found: C, 54.44; H, 3.70; N, 12.70; S, 29.00.

A stirred charge containing 44 g (0.2 mol) of 2-thioxo-3-benzothiazolinepropionitrile and 600 ml of 30% sulfuric acid (by volume) was heated at reflux (114°-116° C.) for 2 hours. After cooling to 25° C., 400 ml of water was added and stirring continued at 25°-30° C., for 15 minutes. The solid was collected by filtration, washed with water until neutral to litmus and air-dried at 50° C. The product, 2-thioxo-3(2H)-benzothiazolepropionic acid, m.p. 164°-165° C., was obtained in 96% yield, after recrystallization from NaOH/HCl, m.p. 167°-168° C.

Anal. Calc'd for $C_{10}H_9NO_2S_2$: C, 50.19; H, 3.79; N, 5.85; S, 26.80. Found: C, 50.09; H, 3.80; N, 5.87; S, 26.87.

EXAMPLE 11

Preparation of 2-Thioxo-3(2H)-Benzothiazolepropanoic Acid, Methyl Ester

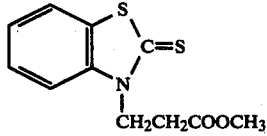

To a stirred solution containing 35.9 g (0.15 mol) of 2-thioxo-3-benzothiazolinepropanoic acid in 600 ml of methyl alcohol, 106.5 g (0.75 mol) of boron trifluoride ether complex was added in one portion. An exothermic reaction set in causing a temperature rise from 20° to 32° C. The stirred solution was heated at reflux for 24 hours. After cooling to 0° C., 1300 ml of a 10% aqueous sodium bicarbonate was added slowly (foaming) at 0°-10° C. until pH 8 was obtained. After stirring for 1 hour at 0°-10° C., the solid was collected by filtration, washed with water until neutral to litmus and air-dried at 25°-30° C. The product 2-thioxo-3(2H)-benzothiazolepropanoic acid methyl esters m.p. 65°-66°, was obtained in 90% yield.

Anal. Calc'd for $C_{11}H_{11}NO_2S_2$: C, 52.15; H, 4.38; N, 5.53; S, 25.31; Found: C, 52.14; H, 4.39; N, 5.52; S, 25.23.

EXAMPLE 12

Preparation of 2-Thioxo-3(2H)-Benzothiazoleacetamide

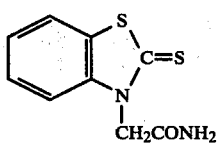

To a stirred slurry, at 25°-30° C., containing 70.0 g (0.276 mol) of the compound of Example 1 in 800 ml of concentrated ammonium hydroxide, was bubbled ammonia gas for 2 hours per day for 4 days. The product 2-thioxo-3(2H)-benzothiazoleacetamide, was collected by filtration, washed with water until neutral to litmus and air-dried at 50° C., m.p. 277°-278° C., yield 91%.

Anal. Calc'd for C9H8N2OS2: C, 48.19; H, 3.60; N, 12.49; S, 28.59; Found: C, 48.16; H, 3.61; N, 12.49; S, 28.50.

EXAMPLE 13

Preparation of
2-Thioxo-3(2H)-Benzothiazolepropanamide

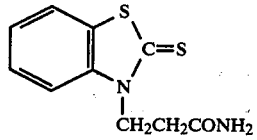

To a stirred solution at 50° C. containing 86 g (0.5 mol) of 2-mercaptobenzothiazole, 60.8 g (0.6 mol) of triethylamine and 500 ml of water, 43 g (0.6 mol) of acrylamide was added in one portion. After stirring at 60°-70° C. for 24 hours, the stirred reaction mixture was cooled to 25° C., the product was collected by filtration, washed with water until neutral and air-dried at 50° C. The product, 2-thioxo-3(2H)-benzothiazolepropanamide, m.p. 226°-227° C., was obtained in 77% yield.

Anal. Calc'd for C10H10N2OS2: C, 50.40; H, 4.23; N, 11.75; S, 26.91; Found: C, 50.28; H, 4.28; N, 11.72; S, 26.79.

EXAMPLE 14

Preparation of
5-Chloro-2-Thioxo-3(2H)-Benzothiazolepropanamide

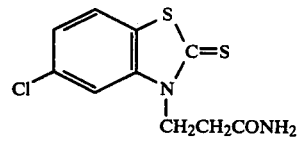

The compound of this example was prepared according to the procedure described in Example 13 except that 5-chloro-2-mercapto-benzothiazole was used as the starting material. The product, 5-chloro-2-thioxo-3(2H)-benzothiazolepropanamide, m.p. 215°-217° C. was obtained in 99% yield.

Anal. Calc'd for C10H9ClN2OS2: C, 44.03; H, 3.33; Cl, 13.00; N, 10.27; S, 23.51; Found: C, 43.98; H, 3.39; Cl, 12.93; N, 10.22; S, 23.47.

EXAMPLES 15-23

A stirred slurry containing 17.8 g (0.07 mol) of 3-(carbethoxymethyl)benzothiazoline-2-thione [C. H. Chen, ORGANIC PREPARATIONS AND PROCEDURES, Inst. 8(1), 1-5 (1976)] and 1 to 2.3 moles of the appropriate amine was stirred at 25°-30° C. for the time period specified in Table II. After the addition of 800 ml of water, stirring was continued at 25°-30° C. for 30 minutes. The solid was collected by filtration, washed with water until neutral to litmus and air-dried at 25°-30° C. The data are summarized in Table II. In the examples described in Table II, T is hydrogen and x is one.

TABLE II

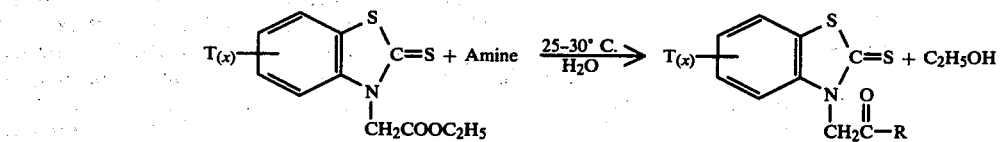

| Ex. No. | Amine | Grams of Amine | Moles | Reaction Time Days | M.P. °C. | % Yld. | % C Calc'd | % C Found | % H Calc'd | % H Found | % N Calc'd | % N Found | % S Calc'd | % S Found |
|---|---|---|---|---|---|---|---|---|---|---|---|---|---|---|
| 15 | 40% CH3NH2 | 177 | 2.3 | 1 | 240-1[a] | 84 | 50.40 | 50.44 | 4.23 | 4.26 | 11.75 | 11.72 | 26.91 | 26.88 |
| 16 | 25% (CH3)2NH | 360 | 2.0 | 3 | 187-9[a] | 45 | 52.35 | 52.36 | 4.79 | 4.74 | 11.10 | 10.37 | 25.41 | 25.73 |
| 17 | HN⟩+ 50 ml H2O | 71 | 1.0 | 3 | 223-4[b] | 82 | 56.09 | 56.18 | 5.07 | 5.09 | 10.06 | 10.05 | 23.03 | 23.00 |
| 18 | 70% C2H5NH2 | 130 | 2.0 | 1 | 219-21[c] | 50 | 52.35 | 52.24 | 4.79 | 4.83 | 11.10 | 11.07 | 25.41 | 25.33 |
| 19 | 65% CH3O(CH2)2NH2 | 231 | 2.0 | 3 | 174-5[d] | 95 | 51.04 | 51.00 | 5.00 | 5.00 | 9.92 | 9.92 | 22.71 | 22.67 |
| 20 | C3H7NH2 + 40 ml H2O | 118 | 2.0 | 1 | 171-3[e] | 22 | 54.11 | 54.10 | 5.30 | 5.32 | 10.52 | 10.50 | 24.07 | 24.07 |
| 21 | HN⟩+ 50 ml H2O | 170 | 2.0 | 3 | 180-2[e] | 34 | 57.90 | 57.43 | 4.86 | 5.52 | 9.65 | 9.56 | 22.08 | 21.90 |
| 22 | CH3O(CH2)3NH2 + 50 ml H2O | 178 | 2.0 | 2 | 147-8[d] | 68 | 52.68 | 52.66 | 5.44 | 5.44 | 9.45 | 9.43 | 21.63 | 21.59 |
| 23 | C2H5O(CH2)2NH2 + | 110 | 1.2 | 2 | 162-4[d] | 98 | 52.68 | 52.73 | 5.44 | 5.44 | 9.45 | 9.40 | 21.63 | 21.50 |

TABLE II-continued

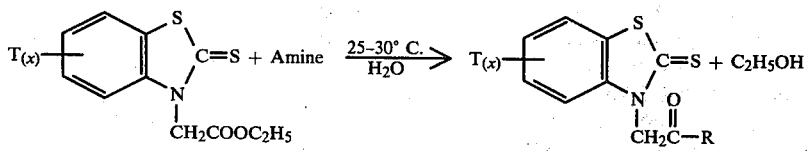

| Ex. No. | Amine | Grams of Amine | Moles | Reaction Time Days | M.P. °C. | % Yld. | % C Calc'd | Found | % H Calc'd | Found | % N Calc'd | Found | % S Calc'd | Found |
|---|---|---|---|---|---|---|---|---|---|---|---|---|---|---|
| | 25 ml H₂O | | | | | | | | | | | | | |

[a] Recrystallization from methyl alcohol
[b] Recrystallization from DMF
[c] Recrystallization from isopropyl alcohol/DMF (6:1)
[d] Recrystallization from toluene
[e] Recrystallization from isopropyl alcohol

EXAMPLE 24

Preparation of 1-Methylhydrazide-2-Thioxo-3(2H)-Benzothiazoleacetic Acid

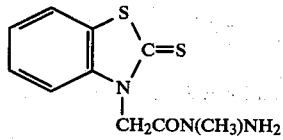

A charge containing 16.8 g (0.07 mol) of Example 1, 92 g (2.0 mol) of N-methyl hydrazine and 100 ml of water was stirred at 25°-30° C. for 4 days. After the addition of 600 ml of water, stirring was continued at 25°-30° C. for 30 minutes. The product was collected by filtration, washed with water until neutral to litmus and air-dried at 25°-30° C. The product, 1-methylhydrazide-2-thioxo-3(2H)-benzothiazoleacetic acid, m.p. 147°-149° C., was obtained in 56% yield; after recrystallization from methyl alcohol, m.p. 159°-161° C.

Anal. Calc'd for $C_{10}H_{11}N_3OS_2$: C, 47.41; H, 4.38; N, 16.59; S, 25.31; Found: C, 47.46; H, 4.38; N, 16.58; S, 25.24.

EXAMPLE 25

Preparation of Hydrazide, 2-Thioxo-3(2H)-Benzothiazoleacetic Acid

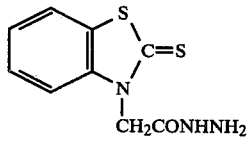

A charge containing 38 g (0.15 mol) of Example 1, 33.8 g (1.0 mol) of 95% hydrazine and 300 ml of water was stirred at 25°-30° C. for 6 days. After the addition of 1 liter of water, stirring was continued at 25°-30° C. for 10 minutes. The product was collected by filtration, washed with water until neutral to litmus and air-dried at 25°-30° C. The product, 2-thioxo-3(2H)-benzothiazole-acetic acid, hydrazide, m.p. 214°-215° C., was obtained in 99% yield; after recrystallization from methyl alcohol, m.p. 222°-223° C.

Anal. Calc'd for $C_9H_9NO_3S_2$: C, 45.17; H, 3.79; N, 17.56; S, 26.80; Found: C, 45.20; H, 3.80; N, 17.55; S, 26.76.

As has been noted, the compounds of the present invention are active as leguminous plant growth regulants. The term "active ingredient" is used herein to describe the novel N-substituted thioxobenzothiazolines of the formula previously described. These compounds have been found to produce a variety of plant growth regulatory responses when applied to leguminous crop plants, for example, soybean (*Glycine max*). The terms "plant growth regulant effect", "plant growth regulation" or words to that effect, are used in this specification and in the claims to mean the causation by the chemicals of the present invention, of a variety of plant responses which achieve a promotion, inhibition or modification of any plant physiological or morphological process. It should additionally be recognized that various plant responses may also result from a combination or sequence of both physiological and morphological factors.

The plant growth regulant effects which may be produced in leguminous plants using the method of the present invention are probably most readily observable as changes in the size, shape, color or texture of the treated plant or any of its parts. Similarly, changes in the quantity of the plant fruit or flowers are also quite apparent from visual inspection. The above changes may be characterized as an acceleration or retardation of plant growth, stature reduction, leaf or canopy alteration, increased branching, tillering, terminal inhibition, increased flowering or fruit set, increased root growth, axillary bud development or inhibition, delayed budding, defoliation, desiccation, delayed senescence, prolonged dormancy, increased cold hardiness, delayed or accelerated ripening, and the like.

Although many of the above modifications are per se desirable, it is most often the ultimate effect of such modifications on the economic factor that is of primary significance. For example, reducing the physical size of each plant in a field permits the growing of more plants per unit area and leads to more efficient use of crop land. Many plants of reduced stature are more tolerant of drought and cold temperatures and are more resistant to pest infestations and to lodging. Reduction in the maturation rate on portions of a crop permits an extended harvest period at peak yield and more efficient use of subsequent crop processing equipment. Suppression of vegetative growth at the appropriate stage of the plant's development may result in increased energy available for utilization in reproductive development so that, for example, more fruit or larger fruit is formed.

Increased plant dry matter accumulation is a valuable plant growth regulant response which can occur in conjunction with morphological changes or can be the sole plant growth response detected. Increased dry matter accumulation is the physically measurable manifestation of increased plant photosynthetic activity. Most plants capture no more than 1 to 3 percent of the solar energy they receive. Present knowledge suggests that it is theoretically possible to increase this rate to approximately twelve percent. Enhancement of photosynthesis at the appropriate stage of the plant's growth and development may enable the plant to fix more carbon dioxide resulting in the production of increased amounts of carbohydrate, amino acids, etc., which could be available for utilization in the plant's reproductive activities, leading to increased crop yields.

It is to be understood that the regulation of desirable crop plants in accordance with the instant invention does not include the total inhibition or the killing of such plants. Although phytotoxic amounts of the materials disclosed herein might be employed to exert a herbicidal (killing) action, it is contemplated here to employ only plant regulating amounts of such materials in order to modify the normal sequential development of the treated plant to agricultural maturity. The application of a plant regulating amount may be applied to plants in sequence at various stages of the plants' development to obtain various desirable responses. As may be expected, and as is apparent to those skilled in the art, such plant regulating amounts will vary, not only with the material selected, but also with the modifying effect desired, the species and its stage of development, the plant growth medium and whether a permanent or transitory effect is sought.

In accordance with this invention it has been found that desirable modification of leguminous crop plants is achieved by applying the above-described plant regulants to the "plant" or plant "habitat". The term "plant" is understood herein to include the seeds, emerging seedlings, roots, stems, leaves, flowers, fruits or other plant parts. The term "habitat" is understood herein to mean the environment of the plant such as the plant growing medium, e.g., the soil.

In the practice of the invention, the active ingredient can be used alone or in combination with a material referred to in the art as an adjuvant in either liquid or solid form. To prepare plant growth regulating compositions, the active ingredient is admixed with an adjuvant including diluents, extenders, carriers and conditioning agents to provide compositions in the form of finely-divided particulate solids, granules, pellets, wettable powders, dusts, solutions and aqueous dispersions or emulsions. Thus, the active ingredient can be used with an adjuvant such as a finely-divided particulate solid, a solvent liquid of organic origin, water, a wetting agent, dispersing agent or emulsifying agent or any suitable combination of these.

Illustrative finely-divided solid carriers and extenders which are useful in plant growth regulating compositions of this invention include the talcs, clays, pumice, silica, diatomaceous earth, quartz, Fullers earth, sulfur, powdered cork, powdered wood, walnut flour, chalk, tobacco dust, charcoal and the like. Typical liquid diluents include Stoddard solvent, acetone, alcohols, glycols, ethyl acetate, benzene and the like. The plant growth regulating compositions of this invention, particularly liquids and wettable powders, usually contain one or more surface-active agents in amounts sufficient to render a given composition readily dispersible in water or in oil. The term "surface-active agent" is understood to include wetting agents, dispersing agents, suspending agents and emulsifying agents. Such surface-active agents are well-known and reference is made to U.S. Pat. No. 2,547,724, Columns 3 and 4, for detailed examples of the same.

Generally, the active ingredients are applied in the form of a composition containing one or more adjuvants which aid in the application of a uniform distribution of the active ingredient. The application of liquid and particulate solid compositions of the active ingredient can be carried out by conventional techniques utilizing for example, spreaders, power dusters, boom and hand sprayers and spray dusters. The compositions can also be applied from airplanes as a dust or spray. Should the application of the plant growth composition to the plant growth medium be desired, this is accomplished by incorporating the compositions in the soil or other media in the area where modifications of the plant is desired.

Compositions of this invention generally contain from about 5 to 95 parts active ingredient, about 1 to 50 parts surface active agent and about 5 to 94 parts solvent, all parts being by weight based on the total weight of the composition.

In selecting the appropriate rate of application of the active ingredient, it will be recognized that precise rates will also be dependent upon the mode of application, such as soil incorporation, band application, pre-plant seed treatment and various other factors known to those skilled in the art. In foliar treatment for the regulation of plant growth, the active ingredients are applied in amounts of from about 0.05 to about 10 pounds per acre. Preferred are foliar applications of from 0.05 to 5 pounds of the active ingredient per acre. In application to the soil habitat of germinant seeds, emerging seedlings and established vegetation for the regulation of plant growth, the active ingredients are applied in amounts of from 0.1 to about 10 pounds per acre or more. The application to the soil of from 0.1 to about 5 pounds of active ingredient per acre is preferred. Foliar application to plants beginning to blossom are preferred over other types of applications.

In accordance with the practice of the invention, plant growth regulating compositions were formulated utilizing the N-substituted-thioxobenzothiazolines of the present invention as the active ingredient. The plant growth regulating properties of the compounds of the invention are illustrated by the test set forth in Example 26.

EXAMPLE 26

A number of soybean plants, variety Williams, were grown from seeds in plastic pots in the greenhouse for a period of one week, at which time the plants were thinned to one plant per pot. When the second trifoliate leaft (three weeks) was fully expanded, the plants were treated with a solution of the active ingredient in acetone and water containing Tween 20 surfactant. When the fifth trifoliate leaf (four to five weeks) was fully expanded, the treated plants were compared with the non-treated control plants and the observations recorded. Table III below, summarizes the results and observations made in accordance with the above procedure when the N-substituted thioxobenzothiazolines of the present invention were utilized as the active ingredient at several application rates.

may be resorted to without departing from the spirit and scope thereof and it is understood that such equivalent embodiments are intended to be included herein.

TABLE III

| Compound of Ex. No. | RATE Lbs/A | RATE Kg/H | % Dry* Weight | Response |
|---|---|---|---|---|
| 5 | 0.1 | 0.14 | 87 | Stem distortion, leaf alteration, leaf inhibition, leaf alteration new growth. |
|  | 0.5 | 0.56 | 13 | Stature reduction, stem distortion, leaf alteration, leaf inhibition, leaf alteration new growth. |
|  | 2.5 | 2.80 | 39 | Stature reduction, epinasty, leaf alteration, leaf inhibition, leaf alteration new growth. |
| 11 | 0.1 | 0.14 | 106 | No response noted. |
|  | 0.5 | 0.56 | 110 | Leaf distortion, leaf inhibition, leaf alteration new growth, slight leaf burn. |
|  | 2.5 | 2.80 | 77 | Leaf distortion, leaf inhibition, leaf distortion new growth, leaf alteration new growth, moderate leaf burn. |
| 11 | 0.1 | 0.14 | 93 | No response noted. |
|  | 0.5 | 0.56 | 93 | Leaf alteration. |
|  | 2.5 | 2.80 | 77 | Leaf distortion, leaf inhibition, leaf alteration, leaf alteration new growth, slight leaf burn. |
| 4 | 0.1 | 0.14 | 76 | Leaf alteration, leaf inhibition, altered canopy. |
|  | 0.5 | 0.56 | 63 | Stature reduction, stem distortion, leaf inhibition, leaf alteration, inhibition of apical development. |
|  | 2.5 | 2.80 | 28 | Stature reduction, epinasty, leaf alteraton, leaf inhibition, inhibition of apical development. |
| 1 | 0.1 | 0.14 | 78 | Leaf alteration, leaf inhibition, altered canopy, axillary bud development, leaf alteration new growth. |
|  | 0.5 | 0.56 | 45 | Stature reduction, leaf alteration, leaf inhibition, altered canopy, inhibition of apical development. |
| 1 | 2.5 | 2.80 | 20 | Stature reduction, epinasty, leaf alteration, leaf inhibition, inhibition of apical development, slight leaf burn. |
| 3 | 0.1 | 0.14 | 86 | Leaf alteration new growth. |
|  | 0.5 | 0.56 | 94 | Leaf inhibition, leaf alteration growth. |
|  | 2.5 | 2.80 | 80 | Leaf inhibition, leaf alteration new growth, inhibition of apical development, altered canopy. |
| 2 | 0.1 | 0.14 | 82 | Leaf alteration, leaf alteration new growth. |
|  | 0.5 | 0.56 | 31 | Leaf alteration, leaf inhibition, stem distortion, inhibition of apical development, stature reduction. |
|  | 2.5 | 2.80 | 23 | Stature reduction, epinasty, leaf alteration, leaf inhibition, inhibition of apical development, slight leaf burn. |
| 10 | 0.1 | 0.14 | 84 | No response noted. |
|  | 0.5 | 0.56 | 86 | Leaf distortion, slight leaf burn. |
|  | 2.5 | 2.80 | 91 | Stature reduction, altered canopy, leaf distortion, leaf inhibition, leaf distortion new growth, moderate leaf burn. |
| 21 | 0.1 | 0.14 | 90 | No response noted. |
|  | 0.5 | 0.56 | 101 | No response noted. |
|  | 2.5 | 2.80 | 93 | Leaf alteration, leaf inhibition, leaf alteration new growth, slight leaf burn. |
| 18 | 0.1 | 0.14 | 95 | No response noted. |
|  | 0.5 | 0.56 | 102 | No response noted. |
|  | 2.5 | 2.80 | 66 | Stature reduction, inhibition of apical development, leaf distortion, stem distortion, leaf inhibition, moderate leaf burn. |
| 16 | 0.1 | 0.14 | 85 | Leaf alteration. |
|  | 0.5 | 0.56 | 97 | Leaf alteration, leaf alteration new growth. |
|  | 2.5 | 2.80 | 85 | Leaf alteration, leaf alteration new growth, leaf inhibition. |
| 17 | 0.1 | 0.14 | 83 | Leaf distortion, leaf alteration new growth, slight leaf burn. |
|  | 0.5 | 0.56 | 118 | Leaf distortion, leaf alteration new growth, slight leaf burn. |
|  | 2.5 | 2.80 | 101 | Leaf inhibition, leaf distortion, leaf alteration new growth, slight leaf burn. |
| 12 | 0.1 | 0.14 | 75 | Leaf alteration, leaf inhibition, leaf alteration new growth. |
|  | 0.5 | 0.56 | 83 | Leaf alteration, leaf inhibition, leaf alteration new growth. |
|  | 2.5 | 2.80 | 74 | Leaf alteration, leaf inhibition, leaf alteration new growth, altered canopy, slight leaf burn. |
| 15 | 0.1 | 0.14 | 84 | No response noted. |
|  | 0.5 | 0.56 | 92 | Leaf distortion, leaf alteration new growth, slight leaf burn. |
|  | 2.5 | 2.80 | 83 | Leaf distortion, leaf alteration new growth, leaf inhibition, slight leaf burn. |
| 25 | 0.1 | 0.14 | 99 | No response noted. |
|  | 0.5 | 0.56 | 87 | Leaf alteration new growth. |
|  | 2.5 | 2.80 | 77 | Leaf alteration, leaf alteration new growth. |

*Calculated as percent of control

The N-substituted thioxobenzothiazoline compounds described herein exhibit unexpected properties when used to regulate the growth of leguminous crop plants, especially soybean (*Glycine max*).

Although this invention has been described with respect to specific modifications, the details thereof are not to be construed as limitations, for it will be apparent that various equivalents, changes and modifications

I claim:
1. A compound of the formula

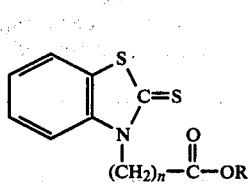

wherein:
n is 1 or 2;

R is hydrogen, $C_{1-5}$ alkyl, halo $C_{1-5}$ alkyl, $C_{2-5}$ alkenyl, halo $C_{2-5}$ alkenyl, or agriculturally acceptable salts; provided that when n is equal to 1, R may not equal hydrogen or ethyl.

2. A compound according to claim 1 wherein n is 1.
3. A compound according to claim 1 wherein n is 2.
4. A compound according to claim 3 wherein R is hydrogen, lower alkyl, halo (lower) alkyl, lower alkenyl or halo (lower) alkenyl.

* * * * *